United States Patent [19]

Partridge

[11] 4,331,158
[45] May 25, 1982

[54] CARDIAC AMPLIFIER SYSTEM WITH LOW TRANSIENT FAST SWITCHING

[75] Inventor: Leslie W. Partridge, Janesville, Wis.

[73] Assignee: The Burdick Corporation, Milton, Wis.

[21] Appl. No.: 180,158

[22] Filed: Aug. 21, 1980

[51] Int. Cl.³ .............................................. A61B 5/04
[52] U.S. Cl. ...................................... 128/709; 128/902
[58] Field of Search .............. 128/695, 696, 709, 710, 128/902

[56] References Cited

U.S. PATENT DOCUMENTS 2,865,366 12/1958 Partridge ............................ 128/709
3,533,003 10/1970 Plaszczywski et al. ............ 128/902

Primary Examiner—William E. Kamm
Attorney, Agent, or Firm—Mason, Kolehmainen, Rathburn & Wyss

[57] ABSTRACT

A cardiac amplifier system with several patient electrodes includes an amplifier with a capacitor coupled input and a switch for coupling different ones of the patient electrodes to the amplifier. A circuit including a time delay, a pair of sequentially operated controlled conduction devices and a resistive network shunts the amplifier input and charges the coupling capacitors in a controlled fashion when the selector switch is operated to prevent switching transients from being applied to the amplifier.

16 Claims, 1 Drawing Figure

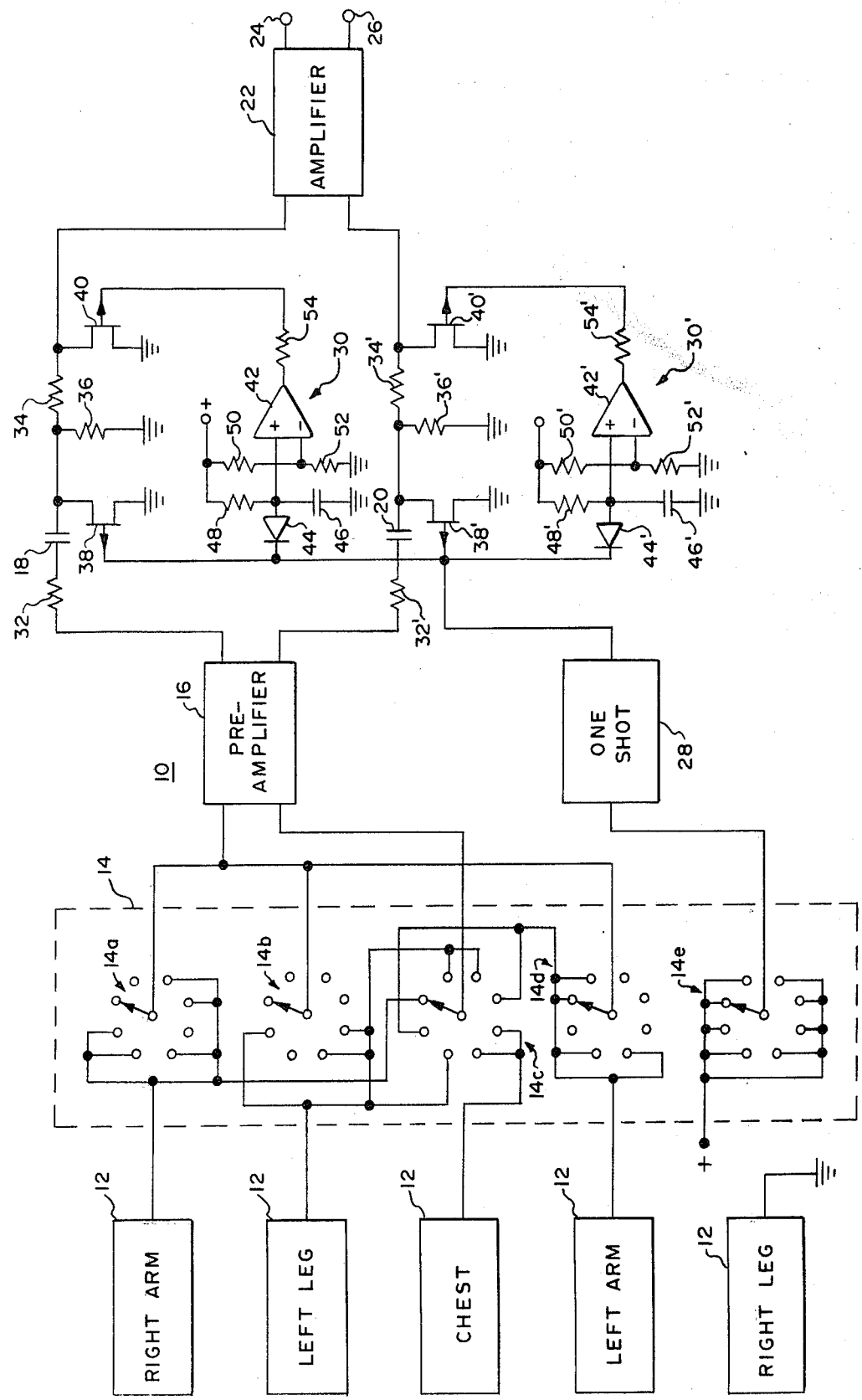

CARDIAC AMPLIFIER SYSTEM WITH LOW TRANSIENT FAST SWITCHING

BACKGROUND OF THE INVENTION

1. Field of the Invention

The present invention relates to cardiac amplifier systems that permit rapid switching between various pairs of patient electrodes. Such an amplifier system can be used in electrocardiographs, heart monitoring systems and other systems that monitor electrical activities of a patient.

2. Description of the Prior Art

Fast switching amplifier systems are known. One such system is disclosed in U.S. Pat. No. 3,477,421 issued to the inventor of the present invention and assigned to the same assignee. The system of the aforesaid U.S. Pat. No. 3,477,421, which is incorporated herein by reference, utilizes a switching transistor to short the input of the amplifier during switching in order to prevent the amplifier from being overdriven by the switching transients and to permit the coupling capacitor to be discharged during the switching operation.

While this system does reduce the amplitude of the switching transients substantially there will be some baseline shift if the switching occurs during a large amplitude portion of the heart wave signal, such as, the peak of the R wave.

SUMMARY OF THE INVENTION

Accordingly, it is an object of the present invention to overcome many of the disadvantages of the prior art systems.

It is another object of the invention to eliminate baseline shift when switching occurs during a high amplitude portion of the heart complex, such as the R wave.

It is another object of the present invention to provide a high speed switching cardiac amplifier system.

It is still another object of the present invention to provide a capacitor coupled amplifier system that has controlled charge and discharge of the coupling capacitor to minimize transients when patient electrodes are switched.

It is yet another object of the present invention to provide a two-step discharge cycle for the coupling capacitor to optimize switching speed and minimize transients.

In accordance with a preferred embodiment of the invention, a cardiac amplifier system employs a plurality of patient electrodes and a selector switch movable to different positions for selectively connecting various ones of the patient electrodes to the amplifier system. A coupling capacitor is used to apply the signal, which may be preamplified, from the selected electrodes to the amplifier. A pair of controlled conduction devices are electrically coupled to the coupling capacitor and to the amplifier, and control the conduction of the controlled conduction devices in response to the operation of the selector switch to prevent the application of undesirable transients to the amplifier. A resistive network is coupled to the coupling capacitor in order to provide controlled charging and discharging of the capacitor, and to further attenuate the transients.

BRIEF DESCRIPTION OF THE DRAWING

These and other objects and advantages of the present invention will become readily apparent upon consideration of the following specification and attached drawing, wherein:

The single FIGURE is a schematic and block diagram of the cardiac amplifier system according to the present invention.

DETAILED DESCRIPTION OF THE PREFERRED EMBODIMENT

Referring now to the drawing, there is illustrated a cardiac amplifier system designated as a whole by the reference numeral 10 and embodying the features of the present invention, and although the invention is illustrated in a cardiac amplifier embodiment, it is also applicable to other capacitor coupled amplifier systems. The system 10 includes five patient electrodes 12, one for each arm and leg and one for the chest of a patient, as labelled on the drawing. One of the patient electrodes is grounded and the others are connected to a lead selector switch generally designated by the reference numeral 14, and having five sections designated by reference numerals 14a through 14e. Input signals from the lead selector switch 14 are preamplified in a preamplifier 16 and are coupled through a pair of coupling capacitors 18 and 20 and other circuitry, which will be described in a subsequent portion of the specification, to an amplifier 22. Cardiac signals from the amplifier 22 appear at a pair of output terminals 24 and 26 and may be used for producing an electrocardiograph record, or for other types of monitoring.

The lead selector switch 14 is operable to a number of different positions for changing the input connections to the amplifier 22, as will readily be understood by those skilled in the art. During switching, undesirable transients resulting, for example, from differences in skin potential or as a result of switching during a high amplitude portion of the cardiac wave, such as the R wave, can be coupled through the capacitors 18 and 20 to the amplifier 22. As a result, the accuracy of the signal provided at the output terminals 24 and 26 is disturbed for a period of time. In addition, the transients may be large enough to overdrive the equipment connected to the output terminals 24 and 26, and may even be harmful to equipment such as a mechanical electrocardiograph. Therefore, in accordance with an important feature of the present invention, a pair of muting circuits, generally designated by the reference numerals 30 and 30', are controlled by a control circuit 28 in response to the operation of the selector switch 14, and serve to reduce the amplitudes of any switching transients applied to the inputs of the amplifier 22 to a level such that they do not affect the accuracy of the signals provided by the amplifier 22. The control circuit 28 may take several forms including a relay or various tube or transistor circuits, but in the illustrated embodiment, a monostable multivibrator, or one shot, is used as the control circuit 28.

With respect to the selector switch, it may be desirable to substitute an electronic multiplex switch. The switching logic signal for the one shot 28 may then be derived from the logic signals addressing the multiplexer. In this way, the poor switching tolerances of the mechanical switch are obviated.

The patient electrodes 12 may be of any conventional construction, and may be connected to the remainder of the apparatus through a plug and socket type of receptacle (not shown). The right leg electrode is connected to ground and the other electrodes are connected to the lead selector switch 14. With respect to these other four electrodes, it may be desirable to interpose a suitable isolating circuit between the electrode and the switch. Such a circuit is particularly important to those positions of the switch in which so-called augmented or so-called V-connections are made, because in these connections, two or more electrodes are coupled in common to one input terminal of the preamplifier.

With respect to all five electrodes, it may be desirable to interpose a suitable isolation circuit between electrodes and ground. Such a circuit is important in providing greater electrical safety for the patient.

The selector switch 14 is effective to change the input connections to the amplifier stage 22, and includes the five sections designated as 14a, 14b, 14c, 14d and 14e. Each section includes a movable switch contact or wiper contact engageable with any one of a plurality of six contacts. In addition, the movable contacts of each section of the switch are ganged together for simultaneous operation, as indicated on the drawing. For example, the lead selector switch 14 may comprise a rotary switch of the type including several wafer elements mounted along an operating shaft or an electronic switch being a multiplex type integrated circuit.

The fixed contacts of the switch sections 14a, 14b, 14c and 14d are selectively connected to different ones of the patient electrodes 12 for the right arm, left leg, chest and left arm. The different positions of the lead selector switch 14 are effective to provide different types of input connections to the amplifier 22. In one type of connection, one patient electrode is connected to each side of the preamplifier 16. In the so-called augmented connection (one of which is illustrated in the drawing), two of the patient electrodes are connected together and these interconnected electrodes are connected to one side of the preamplifier input, the other input of the preamplifier 16 being connected to a single electrode. In a third, so-called V-connection, three electrodes are connected to one input of the preamplifier 16, and the other input of the preamplifier is connected to the chest electrode. As can be seen from the number of possible interconnections of the various electrodes 12, the probability of providing a disruptive switching transient is quite high. Also, the probability of switching during a high amplitude portion of the cardiac signal, such as the R wave, is greater for a high speed switching system that monitors many different cardiac complexes in an automatic sequential manner.

The preamplifier 16 may be of any desired conventional construction, and may include one or more stages of amplification including either transistors, integrated circuits or vacuum tubes. The preamplifier 16, preferably of the push-pull type, includes one input connected to the wiper contact of the switch section 14c and another input connected in common to the wiper contacts of the switch sections 14a, 14b and 14d.

The amplifier 22 may also be of any desired conventional construction and may comprise a push-pull DC amplifier including one or more transistors, integrated circuits or vacuum tube amplifying stages. The two input leads of the amplifier 22 are coupled to the output of the preamplifier 16 by the coupling capacitors 18 and 20.

Each patient electrode 12 developes a "skin potential" by interaction with the patient's body, the magnitude of which depends on the electrode material and surface condition, and it is normal for the skin potential at different electrodes to differ. Thus, in each position of the selector switch 14, certain quiescent charges are imposed across the capacitors 18 and 20, this charge depending to a great extent on the skin potential of the electrodes selected by the selector switch 14. When the lead selector switch 14 is moved between positions to change the input connections, it is necessary for the charge on the coupling capacitors 18 and 20 to reach a new steady state level before an accurate record is provided at the output terminals 24 and 26.

In addition to the transients caused by the variations in skin potential present at the electrodes 12, other undesirable transients may be introduced during switching, particularly if the switching occurs during a high amplitude peak, such as the R wave, of the electrocardiac wave. These transients are coupled to the amplifier 22 through the coupling capacitors 18 and 20, can interfere with the output signal.

In order to permit the coupling capacitors 18 and 20 to reach their steady state charge condition rapidly upon switching, and in order to prevent the application of undesirable transients to the amplifier 22, the novel muting circuit arrangements of 30 and 30' are provided. It should be noted that because the system is a push-pull system, two identical muting circuits 30 and 30' are provided, one for each lead of the push-pull system; however, it should be noted that if the preamplifier stage and/or an amplifier system having only a single non-common input lead were used, only a single muting circuit would be required. In many modern systems, such a single ended preamplifier is preferable.

More specifically, the muting circuit 30 utilizes three direct current conductive means such as, for example, resistors 32, 34 and 36 to control the rate at which the capacitor 18 is charged or discharged, and a pair of controlled conduction switching devices having main terminals and a control terminal to speed charging or discharging of the capacitor 18 and to prevent the switching transients from being applied to the amplifier 22. In the present embodiment, field effect transistors 38 and 40 are used as the controlled conduction devices, however, various other transistors or various solid state or other switching devices may be used. The field effect transistors 38 and 40 are controlled by the circuit 28 and by a delay circuit comprising an amplifier 42, a diode 44, a capacitor 46 and resistors 48, 50, 52 and 54. The muting circuit 30' utilizes similar components, with analogous components of the circuit 30' being assigned identical reference numerals except that the reference numerals of the components of the circuit 30' will also be primed.

Each of the field effect transistors 38 and 40 (as well as transistors 38' and 40') is normally held in a non-conductive or open condition between its main terminals (source and drain terminals) by control signals coupled to the control electrodes (gate electrodes) thereof from the switch section 14e via the circuit 28 and the circuits including the amplifier 42 (and 42').

More specifically, the circuit 28, which is illustrated in the drawing as a monostable multivibrator, or one shot, is coupled to the wiper of the switch section 14e. The fixed contacts of the switch section 14e are, in the present embodiment, connected to a source of positive potential. Thus, under non-switching conditions, a positive potential is applied to the input of the circuit 28 which provides a positive, or high, output to the circuits 30 and 30', thus maintaining the field effect transistors 38, 38', 40 and 40' non-conductive. However, when a new set of patient electrodes are selected by the lead selector switch 14, the switch 14e is rotated between adjacent fixed positions, and during this rotation, the circuit between the source of positive potential applied to the fixed contacts of the switch section 14e and the base of the transistor 56 is momentarily broken. During this momentary break, the voltage applied to the circuit 28 is zero, and the output of the circuit 28 immediately goes low (e.g., to zero) and remains low for a predetermined time interval such as, for example, 30 milliseconds. The low output of the circuit 28 renders the field effect transistors 38 and 38' conductive, and causes the outputs of the amplifiers 42 and 42' to go low, or relatively negative, in order to render the transistors 40 and 40' conductive. The amplifiers 42 and 42' and associated circuitry then maintain the field effect transistors 40 and 40' conductive for an additional time interval, such as, for example, 100 milliseconds, as determined by the capacity of the capacitor 46 and the values of the resistors 48, 50 and 52, after the output of the circuit 28 goes high. Thus, the amplifier 22 remains muted for a total time interval of only 130 milliseconds.

In order to achieve a total muting time interval of 130 milliseconds or less, a two step discharge process utilizing two devices that are conductive for different time intervals, such as the transistors 38, 38' and 40, 40', are utilized. Also, the values of the coupling capacitors 18 and 20, and the resistors 32, 32', 34, 34' and 36, 36' are carefully controlled, with the values of these components being determined by the nature of the transient being suppressed, the output impedance of the preamplifier 16 and the required low frequency response of the electrocardiograph.

In the illustrated embodiment, the preamplifier 16 has a low impedance, so the charging current through the coupling capacitors when the transistors 38 and 38' are conductive is determined primarily by the resistance of the resistors 32 and 32' and the value of the power supply voltage supplying power to the preamplifier 16. In order to minimize muting time, it is desirable to charge or discharge the capacitors 18 and 20 as rapidly as possible, which requires a low resistance value for the resistors 32 and 32'. However, the output current capacity of the preamplifier 16 is limited, thus, the value of the resistors 32 and 32' must be selected so that the maximum output current capability of the preamplifier 16 is not exceeded. In the present embodiment, the maximum current capability of the preamplifier 16 is approximately 3.33 milliamperes, and the voltage of the power supply (not shown) driving the preamplifier 16 is 10 volts. Thus, the resistance of the resistors 32 and 32' required to limit the output current to 3.33 milliamperes is equal to the power supply voltage divided by the maximum allowable output current, or 10 volts divided by 3.33 milliamperes equals 3,000 ohms.

The capacitance of the capacitors 18 and 20, and the resistances of the resistors 36 and 36' determine the low frequency response of the amplifier. For electrocardiograph purposes, the low frequency response is standardized by defining the product of the capacitance of the capacitor 18 and the resistor 36 (or the capacity of the capacitor 20 and the resistance of the resistor 36') to be equal to 3.6 seconds. Thus, the values of the capacitors 18 and 20 and the resistors 36 and 36' are flexible as long as the product of their values equals 3.6 seconds. In the present embodiment, the capacity of the capacitors 18 and 20 is selected to be 1 microfarad to avoid the use of excessively large and bulky capacitors, and the resistance of the resistors 36 and 36' is selected to be 3.6 megohms to provide the required 3.6 second time constant.

Because of the relatively high current flow through the field effect transistors 38 and 38' immediately following the switching action, a voltage appears across the transistors 38 and 38' as a result of the finite resistance between the drain and source electrodes of those transistors. In order to prevent this voltage from being applied to the amplifier 22, the resistors 34 and 34', and the transistors 40 and 40' serve as a voltage divider network that divides the voltages appearing across the transistors 38 and 38' before they are applied to the inputs of the amplifier 22. Thus, to minimize the amplitude of the voltages applied to the amplifier 22, the resistance of the resistors 34 and 34' should be high compared to the resistances of the transistors 40 and 40' when the transistors 40 and 40' are rendered conductive. However, the resistance of the resistors 34 and 34' should not be so high as to attenuate the cardiac signal being applied to the amplifier 22. In the present embodiment, the resistance of the resistors 34 and 34' is selected to be 100,000 ohms since that value meets the above-described criteria or as well as meeting the requirements to reduce any transient appearing across the mute transistor 38 (and 38') when turned off during a high amplitude portion of the electrocardiograph signal, such as the peak of the R wave.

The value of the resistors 34 and 34' must be chosen to optimize circuit performance by balancing the conflicting requirements of switching at different times during the complex cardiac wave. The value of the resistors 32 and 32', 34 and 34' as well as the time intervals that the transistors 38 and 38' and 40, 40' are rendered conductive must satisfy the following conditions:

1. the start or end of the mute operation must be able to occur during any part of the cardiac complex, or before or after it, without causing excessive baseline shift or an inaccuracy of the signal at the terminals 24 and 26;

2. the time that the transistors 38 and 38' are conductive must allow adequate charge of the capacitors 18 and 20, respectively, with inputs having an amplitude of up to 300 times the cardiac signal voltage;

3. the total time interval during which any of the transistors 38, 38' and 40, 40' is conductive must be shorter than the cardiac signal complex;

4. the load on the circuit must be negligible; and 5. transients caused by switching during a high amplitude portion of the cardiac signal, such as the R wave, must be minimized.

One equation showing the interrelationship between the conflicting requirements, the values of the various components of the muting circuit and the times that each of the controlled conduction devices is rendered conductive is given by below. This equation determines the necessary on-time $T_1$ of transients 38 (or 38') in order to reduce the output transient caused by electrode offset voltages to 1% of the signal voltage:

$$T_1 = \frac{R_{32}C\left(R_{32} + \frac{R_{36}R_{34}}{R_{36} + R_{34}}\right)}{\frac{R_{36}R_{34}}{R_{36} + R_{34}}}$$

$$\left( \ln \frac{VR_{36}}{R_{32} + R_{36}} - \ln e_o{}^3{}_{tr} - \frac{T_2}{C\left(R_{32} + \frac{R_{36}R_{34}}{R_{36} + R_{34}}\right)} \right)$$

wherein signal voltage amplitude is unity, and wherein: $T_2$ equals the total muting time, or the time that the transistors 40 and 40' are rendered conductive which equals 130 milliseconds (maximum allowable time); $R_{32}$ equals the resistance of the resistors 32 and 32' which equals 3,000 ohms as determined above; C equals the capacitance of the capacitors 18 and 20 which equals 1 microfarad as determined above; $R_{36}$ equals the resistance of the resistors 36 and 36' which equals 3.6 megohms as determined above; $R_{34}$ equals the resistance of the resistors 34 and 34' which equals 100,000 ohms (as determined below); V equals the multiple of the amplitude of the cardiac signal voltage that can be handled by the system which equals 300 as a design parameter; and the output transient $e_{o3tr}$ equals 1% or 0.01.

Based on the solution of the above equation utilizing the above parameters, it is determined that the value of $T_1$ equals 0.02787 seconds, which may be conveniently rounded off to the 0.030 seconds or 30 milliseconds previously discussed in the text. However, as can be seen from the above equation, there is no unique solution to the equation, and various values of resistance, capacitance and switching times meet the conditions set forth in the above equation.

A second set of mathematical equations is necessary to determine the best value of $R_{34}$ and $R_{34}'$. The curves obtained from these equations show the transient output voltage versus the value of $R_{34}$ and $R_{34}'$ for various timing conditions of $T_2$ with respect to the timing of the complex signal voltage. Since some of these curves ascend and others descend, the lowest crossover point is chosen for the best value of $R_{34}$ or $R_{34}'$.

Thus, in order to determine whether the optimum combination of parameters has been achieved, one must determine the value of the transient after the output transistors 40 and 40' have been rendered non-conductive at the end of the mute cycle. This can be achieved by use of these equations and curves or by use of a computer simulation where the shape of the waveform being attenuated is computer simulated and various combinations of resistance, capacitance and switching times within the design constraints and the constraints of the equation above are tried, and the optimum combination of parameters may be determined using an iterative process.

Obviously, many modifications and variations of the present invention are possible in light of the above teachings. Thus, it is to be understood that, within the scope of the appended claims, the invention may be practiced otherwise than as specifically described above.

What is claimed and desired to be secured by Letters Patent of the United States is:

1. An amplifier switching system comprising:
a plurality of input leads;
an amplifier having an input;
means including a coupling capacitor coupled to said input for supplying electrical signals to said amplifier;
switching means coupled between said input leads and said coupling capacitor for changing input connections to said amplifier;
first direct current conductive means coupled in series with said coupling capacitor for controlling the flow of current through said coupling capacitor;
second direct current conductive means coupled in series with said coupling capacitor and the input to said amplifier;
a first controlled conduction device having main terminals coupled in series with said first direct current conductive means and said coupling capacitor, said first controlled conduction device also having a control terminal;
a second controlled conduction device having main terminals coupled in series with said first and second direct current conductive means and said coupling capacitor, said second controlled conduction device also having a control terminal;
first means responsive to the actuation of said switching means coupled to the control terminal of said first controlled conduction device for rendering said first controlled conduction device conductive for a first predetermined time interval following the actuation of said switching means; and
second means responsive to the actuation of said switching means coupled to the control terminal of said second controlled conduction device for rendering said second controlled conduction device conductive for a second predetermined time interval.

2. An amplifier switching system as recited in claim 1 wherein said first switching means actuation responsive means includes means for rendering said first controlled conduction device conductive for a time interval different than the time interval said second controlled conduction device is rendered conductive.

3. An amplifier switching system as recited in claim 2 wherein said first and second switching means actuation responsive means include means for rendering said first predetermined time interval shorter than said second predetermined time interval.

4. An amplifier switching system as recited in claim 3 wherein said first and second switching means actuation responsive means include means for rendering said first and second controlled conduction devices conductive substantially simultaneously.

5. An amplifier switching system as recited in claim 4 wherein said first and second direct current conductive means are resistors.

6. An amplifier switching system as recited in claim 1 wherein at least one of said controlled conduction devices is a field effect transistor.

7. An amplifier switching system as recited in claim 6 wherein said first and second controlled conduction devices are field effect transistors.

8. An amplifier switching system as recited in claim 1 wherein said means for applying electrical signals to said amplifier includes a preamplifier having an output impedance lower than the impedance of said first direct current conductive means.

9. An amplifier switching system as recited in claim 1 wherein said amplifier has a predetermined input impedance higher than the impedance of said second direct current conductive means.

10. An amplifier switching system as recited in claim 1 further including third direct current conductive means coupled in parallel with said first controlled conduction device.

11. An amplifier switching system as recited in claim 10 wherein said third direct current conductive means is a third resistor.

12. An amplifier switching system as recited in claim 11 wherein the product of the capacity of said coupling capacitor and the resistance of said resistor does not exceed 3.6 seconds.

13. An amplifier switching system as recited in claim 12 wherein said system includes means for rendering the time interval from the rendering conductive of the first of said controlled conduction devices rendered conductive following actuation of said switching means and the rendering non-conductive of the last of said controlled conduction devices following said actuation of said switching means does not exceed approximately 130 milliseconds.

14. An amplifier switching system as recited in claim 1 wherein said system includes a source of common potential and said first and second controlled conduction devices are electrically coupled to said source of common potential.

15. An amplifier switching system as recited in claim 1 wherein at least one of said controlled conduction devices is a transistor.

16. An amplifier switching system as recited in claim 15 wherein said first and second controlled conduction devices are transistors.

* * * * *